(12) United States Patent
Stoutenburgh et al.

(10) Patent No.: US 10,702,223 B2
(45) Date of Patent: Jul. 7, 2020

(54) IMAGING TABLE FOR GREATER ACCESS TO PATIENT REGION OF INTEREST

(71) Applicant: Epica International, Inc., San Clemente, CA (US)

(72) Inventors: Gregory William Stoutenburgh, San Clemente, CA (US); Mark Dettman, Milledgeville, IL (US)

(73) Assignee: Epica International, Inc., San Clemente, CA (US)

( * ) Notice: Subject to any disclaimer, the term of this patent is extended or adjusted under 35 U.S.C. 154(b) by 59 days.

(21) Appl. No.: 16/000,699

(22) Filed: Jun. 5, 2018

(65) Prior Publication Data

US 2018/0353144 A1 Dec. 13, 2018

Related U.S. Application Data

(60) Provisional application No. 62/516,585, filed on Jun. 7, 2017.

(51) Int. Cl.
*A61B 6/04* (2006.01)
*A61G 13/06* (2006.01)
*A61G 13/10* (2006.01)

(52) U.S. Cl.
CPC .......... *A61B 6/0407* (2013.01); *A61B 6/0442* (2013.01); *A61G 13/06* (2013.01); *A61B 6/0457* (2013.01); *A61G 13/104* (2013.01); *A61G 2210/50* (2013.01)

(58) Field of Classification Search
CPC ................ A61B 6/04; A61B 6/0407
See application file for complete search history.

(56) References Cited

U.S. PATENT DOCUMENTS

| 3,652,851 | A | 3/1972 | Zaalberg | |
| RE36,415 | E | 11/1999 | McKenna | |
| 6,212,251 | B1 * | 4/2001 | Tomura | A61B 6/032 378/15 |
| 6,959,068 | B1 * | 10/2005 | Sommer | A61B 6/032 378/20 |
| 7,545,911 | B2 * | 6/2009 | Rietzel | A61B 6/04 378/205 |

(Continued)

OTHER PUBLICATIONS

PCT International Written Opinion of the International Searching Authority dated Aug. 24, 2018 in corresponding PCT Application No. PCT/US18/36300, inventor Gregory W. Stoutenburgh, et al.

*Primary Examiner* — Yara B Green
(74) *Attorney, Agent, or Firm* — Steptoe & Johnson LLP (57) ABSTRACT

A system and method for providing a radiological imaging system including a table for greater access to patient region of interest. The imaging system includes a gantry defining an analysis zone. A source suitable to emit radiation and at least one detector suitable to receive the radiation are housed within the gantry. The system includes a translating component to translate the gantry in a main direction. The system includes a bed extending along the main direction and having a table top to support a patient, a base, and at least one support member connected between the table top and the base. The table top may translate along the main direction, and at least one support member is adjustable to raise and lower the table top. The table top may also be translating in a direction perpendicular to the main direction in a Y axis or tilted along the Z axis.

14 Claims, 5 Drawing Sheets

(56) References Cited

U.S. PATENT DOCUMENTS

| | | | |
|---|---|---|---|
| 8,424,133 B1* | 4/2013 | Rossi | A61B 6/0442 5/601 |
| 2003/0196268 A1 | 10/2003 | Heimbrock | |
| 2007/0245488 A1* | 10/2007 | Zimbalista | A61G 7/0507 5/86.1 |
| 2010/0172468 A1 | 7/2010 | Gregerson | |
| 2012/0189094 A1* | 7/2012 | Neushul | A61B 6/4266 378/19 |
| 2015/0366519 A1* | 12/2015 | Furuta | G01T 1/2985 600/431 |

* cited by examiner

IMAGING TABLE FOR GREATER ACCESS TO PATIENT REGION OF INTEREST

CROSS-REFERENCE TO RELATED APPLICATIONS

The present application claims the benefit of U.S. Provisional Application No. 62/516,585, filed Jun. 7, 2017, entitled "Imaging Table for Greater Access to Patient Region of Interest" which is herein incorporated by reference in its entirety.

FIELD

The present disclosure relates in general to the field of a radiological imaging system, and in particular, to an imaging table for greater access to patient region of interest and systems/methods incorporating the foregoing.

BACKGROUND

Radiological imaging devices currently available on the market have a standard structure including a flatbed on which a patient is placed in order to perform image scanning of the patient. To keep the patient still during the image scanning and thereby ensure the expected performance of the radiological imaging procedure, the bed is typically fitted with straps to restrain the patient. However, the straps may prevent the passage of the X-rays and thereby the correct visualization of the portions adjacent to the straps.

For this reason, in some imaging procedures, the straps covering a portion of the area of interest are practically unusable, and the patient may be required to stay still or held by the operator, who is therefore exposed to the X-rays. Additionally, the radiological imaging device may require a specific detector for each analysis and can perform only one type of analysis at a time.

As a result, in the case in which a patient needs to undergo several analyses, the patient needs to be taken from the radiological imaging device, placed on a treatment or surgical bed, moved, picked up again and then laid on a second radiological imaging device. Such maneuvers often entail problems for the patient and the procedure, and therefore need to be performed with particular care and expertise. Consequently, the length of time needed to perform the aforementioned maneuvers increases.

Additionally, a patient may need to be repositioned for optimal imaging or to allow personnel, such as a physician, to gain access to the patient region of interest without removing the patient or the bed from the radiological imaging device. However, the bed of existing imaging devices does not allow easy maneuver of patients, especially when the patient is secured to the bed by straps or restraints. Consequently, the length of time needed to perform the aforementioned maneuvers increases.

SUMMARY

Existing limitations associated with the foregoing, as well as other limitations, can be overcome by a system and method including a bed and a radiological imaging device, and a bed for use with a radiological imaging device. Although the bed is described in relation to a radiological imaging device, the bed may be used with other devices. Furthermore, the bed of the current invention may be used as a surgical bed, a treatment bed, and a bed to transport a patient to and from various locations for different procedures.

Briefly, and in general terms, the present disclosure is directed to various embodiments of a radiological imaging system. The radiological imaging system permits the patient to be moved simply and quickly, and reduces risks to the patient. According to one embodiment, the radiological imaging system may be a multimodality imaging device with a circular gantry. The radiological imaging system may include a bed that includes a table that may be put through the gantry of the radiological imaging system. The area of the bed that may be in the imaging area may be radiolucent, and in other embodiments, the entire bed may be made of radiolucent materials. In one embodiment, at least of portion of the bed is made from a material having reduced Hounsfield units (HU) such as, for instance, a composite material with a polymer matrix and fiber reinforcement, yet more specifically, carbon fiber or aramid or glass fiber and matrix in epoxy resin or the like. The radiological imaging system also includes a source suitable to emit radiation and at least one detector suitable to receive the radiation and to be positioned substantially on an opposite side to the source in relation to the bed.

In one embodiment, the imaging area of the gantry extends outside the closed ring (i.e. projected forward to allow clear side access) the clinician would have unobstructed access to three sides of the patient. This may be used with interventional procedures or may allow a portable imaging CT/Fluoroscopy device to be used with the gantry of the imaging system in the 90 degree rotated position with respect to the longitudinal axis of the patient in the bed.

In one embodiment, the bed includes a table top extending along the main direction. The table top supports a patient. The bed also includes a base and at least one support member connected between the table top and the base. With the base in a stationary position, the table top translates along the main direction, and the at least one support member is adjustable to raise and lower the table top. The table top may also be translating in a direction perpendicular to the main direction in a Y axis. Furthermore, the table top may be tilted around an axis defined by the main direction.

In another embodiment, the radiological imaging system includes at least one load-bearing structure to support the bed, the source and the detector. The radiological imaging system may further include at least one retaining apparatus suitable to removably fix one or more load-bearing structures to the bed. This allows the bed to be secured to the one or more load-bearing structures, optionally during a procedure, and then later removed from one or more load-bearing structures after the procedure. After removing the bed from the load-bearing structure, the patient may be transported in the bed to another location. In one embodiment, the at least one retaining apparatus is suitable to fix the load-bearing structure to the bed using a snap-fit attachment. Other types of retaining apparatus may also be used, including Velcro, ties, hooks, screws, removable bolts, clasps, magnets or the like. In other embodiments the bed is not secured to the load-bearing structure, and instead may be locked in place with relation to the floor.

The present disclosure also is directed to a method of obtaining radiological images of a patient. In one embodiment, the method includes placing the patient on a support surface of a bed so the bed contains at least a portion of the patient. In one embodiment, the bed includes a table top extending along the main direction. The table top supports a patient. The bed also includes a base and at least one support member connected between the table top and the base. With the base in a stationary position, the table top translates along the main direction, and the at least one support member is adjustable to raise and lower the table top. The table top may also be translating in a direction perpendicular to the main direction in a Y axis. Furthermore, the table top may be tilted around an axis defined by the main direction. The bed may be made of a radiolucent or radio-transparent material, for example, carbon fiber or any other suitable radio-transparent material.

In one embodiment, the method also includes emitting radiation from a source to a portion of the patient, and receiving the radiation using at least one detector. The at least one detector may be positioned substantially on an opposite side to the source in relation to the bed. Furthermore, it has been contemplated that the bed is adjustable in X, Y, and Z axes.

In certain embodiments, the bed may be designed such that it may be put through the circular gantry of the imaging device and after removing the bed from the radiological imaging system, the patient may be transported in the bed to another location.

Other features and advantages will become apparent from the following detailed description, taken in conjunction with the accompanying drawings, which illustrate by way of example, the features of the various embodiments.

BRIEF DESCRIPTION OF THE DRAWINGS

The teachings claimed and/or described herein are further described in terms of exemplary embodiments. These exemplary embodiments are described in detail with reference to the drawings. These embodiments are non-limiting exemplary embodiments, in which like reference numerals represent similar structures throughout the several views of the drawings, and wherein:

DETAILED DESCRIPTION

Each of the features and teachings disclosed herein can be utilized separately or in conjunction with other features and teachings to provide a radiological imaging system with a bed. Representative examples utilizing many of these additional features and teachings, both separately and in combination are described in further detail with reference to the attached figures. This detailed description is merely intended to teach a person of skill in the art further details for practicing aspects of the present teachings and is not intended to limit the scope of the claims. Therefore, combinations of features disclosed above in the detailed description may not be necessary to practice the teachings in the broadest sense, and are instead taught merely to describe particularly representative examples of the present teachings.

In the description below, for purposes of explanation only, specific nomenclature is set forth to provide a thorough understanding of the present disclosure. However, it will be apparent to one skilled in the art that these specific details are not required to practice the teachings of the present disclosure.

The methods or processes presented herein are not inherently related to any particular computer or other apparatus. Various general-purpose systems, computer servers, or personal computers may be used with programs in accordance with the teachings herein, or it may prove convenient to construct a more specialized apparatus to perform the method steps. The structure for a variety of these systems will appear from the description below. It will be appreciated that a variety of programming languages may be used to implement the teachings of the disclosure as described herein.

Moreover, the various features of the representative examples and the dependent claims may be combined in ways that are not specifically and explicitly enumerated in order to provide additional useful embodiments of the present teachings. It is also expressly noted that all value ranges or indications of groups of entities disclose every possible intermediate value or intermediate entity for the purpose of original disclosure. It is also expressly noted that the dimensions and the shapes of the components shown in the figures are designed to help to understand how the present teachings are practiced, but not intended to limit the dimensions and the shapes shown in the examples.

Figure 1:
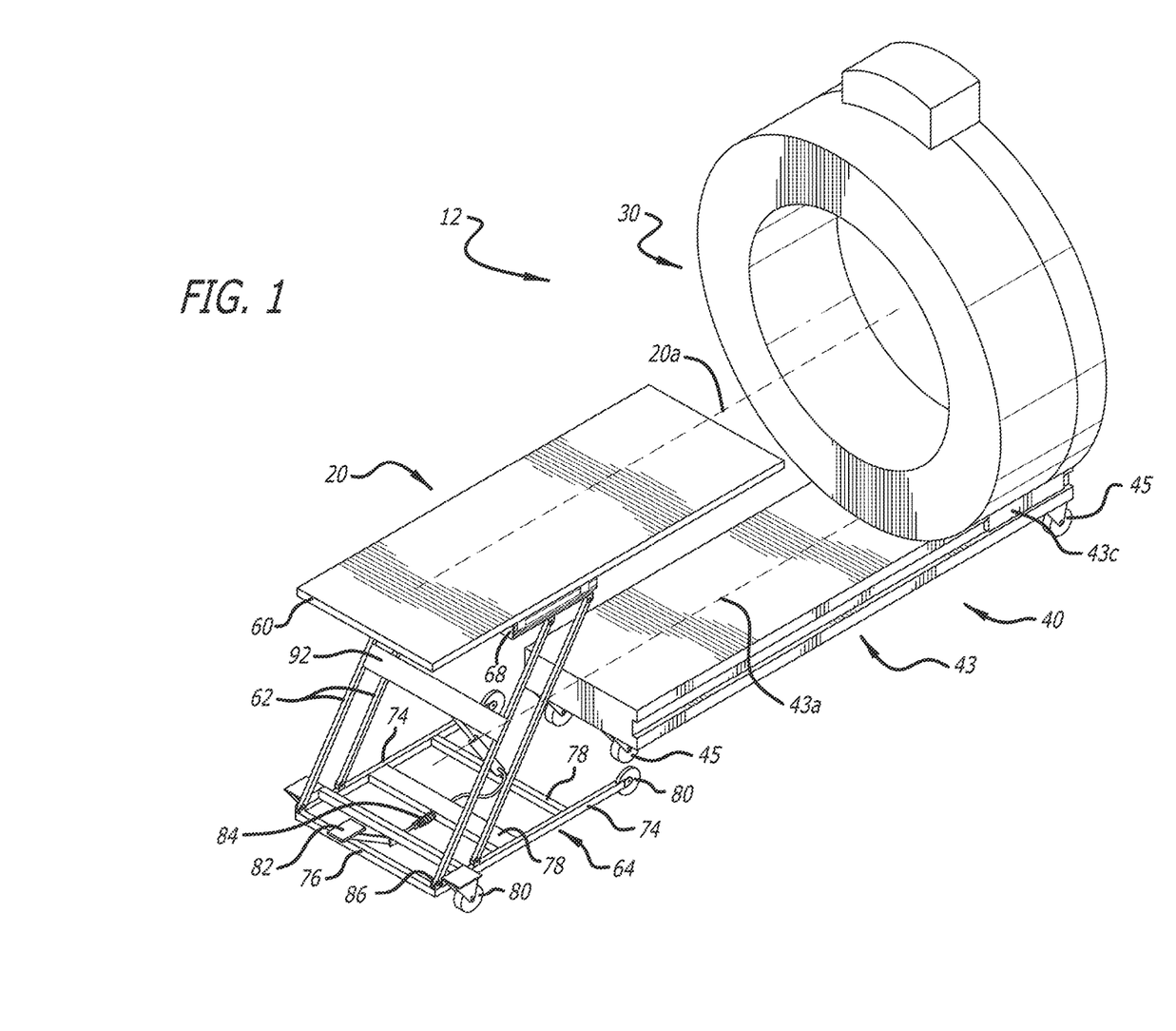
FIG. 1 shows an exemplary radiological imaging system, according to one embodiment.

With reference to FIGS. 1-5, reference numeral 1 denotes a radiological imaging system. The radiological imaging system 1 is useful in both the medical and veterinary applications for performing radiological imaging of at least one portion of the internal anatomy of a patient. In particular, the radiological imaging system 1 is suitable for performing radiological imaging examinations including, but not limited to, X-rays, CT scans, and fluoroscopy. In one embodiment, the imaging system 1 includes a control unit suitable to control the radiological imaging system 1. The system also includes a bed 20 extends along a main direction 20*a* and having a support surface for the patient. A gantry 30 suitable to perform the radiological imaging of at least one portion of the patient and defining an analysis zone 30*a* suitable to house at least a portion of the bed 20. For example, the gantry may have a circular shape as shown in FIG. 1, which is suitable to house at least one portion of the bed 20. Further, the radiological imaging system shown in the embodiment of FIG. 1 includes a load-bearing structure 40 suitable to support the gantry 30.

Figure 5:
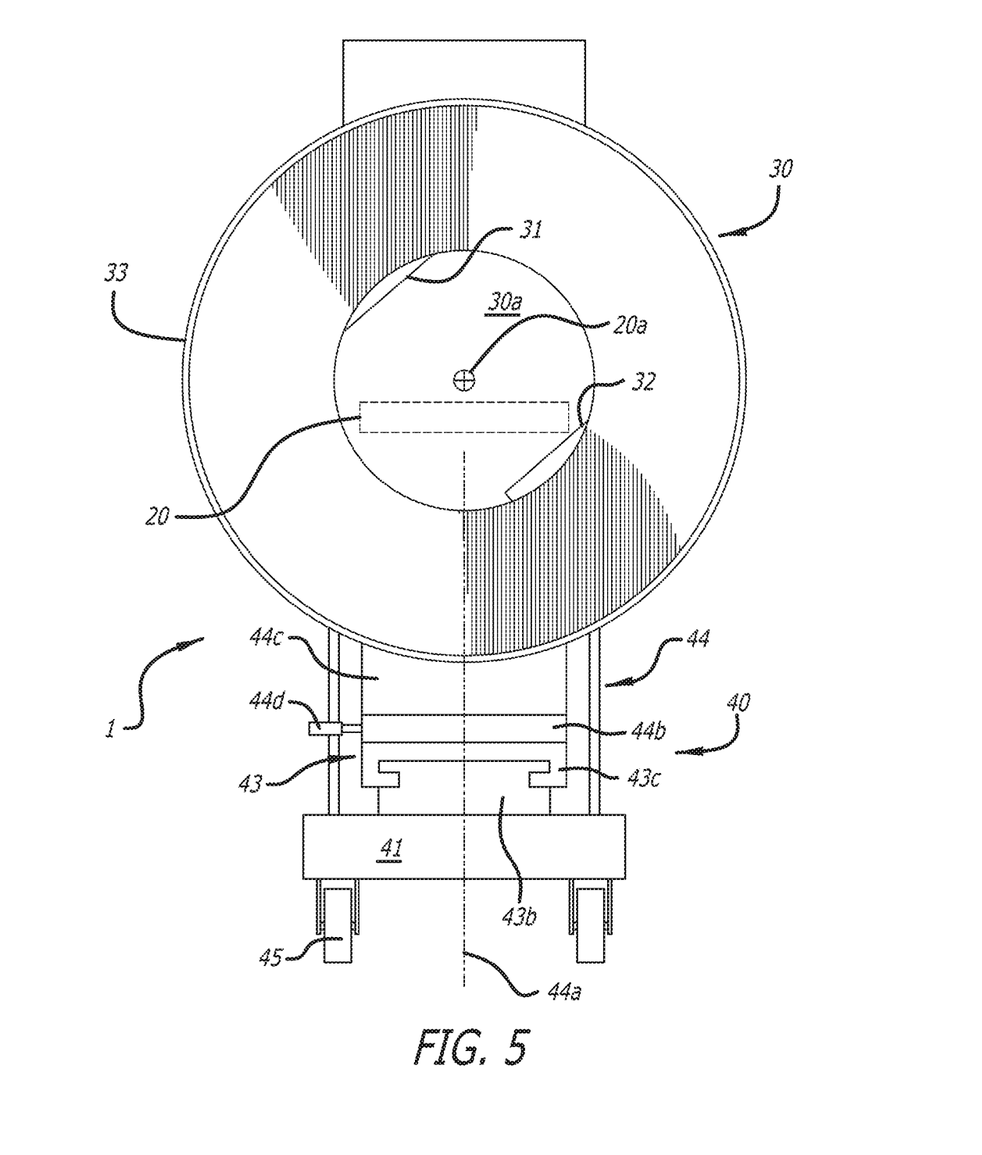
FIG. 5 shows a side elevational view of a radiological imaging system.

As best shown in FIG. 5, the gantry 30 contains various components for performing the radiological scan. Examples of the components contained in the gantry 30 include, but are not limited to the following. A source 31 suitable to emit radiation, for example X-rays. The gantry may also include at least one detector 32 suitable to receive the radiation emitted by the source 31 and suitable to be positioned substantially on the opposite side of the bed 20 to the source as shown in the embodiment of FIG. 5. Further, the gantry may include a housing 33 suitable to contain at least partially the aforementioned components, and the housing may contain addition components as needed. In particular, the detector 32 is suitable to detect the radiation (e.g., X-ray) that has traversed the patient's body during a scan. In one embodiment, the detector 32 may include a sensing element such as a flat panel and/or a linear sensor.

One example of an imaging device is disclosed in U.S. Ser. No. 14/932,806, which is incorporated herein by reference in their entireties, as if set forth fully herein. In one embodiment, the detector 32 detects radiation when performing at least one of tomography, fluoroscopy, radiography, and multimodality and generates data signals based on the radiation received. Furthermore, in one embodiment, at least one detector includes at least one flat panel sensor and/or at least one linear sensor. In an example embodiment in which the at least one detector is a flat panel sensor, the flat panel sensor is selectably operable in at least a flat panel mode and a linear sensor mode obtained, for example, by activating one or more pixel rows that are, preferably, substantially perpendicular to the axis of the bore. In a further example embodiment herein, in the flat panel mode, the sensor performs at least one of fluoroscopy and tomography, and, in the linear sensor mode, performs at least one of radiography and tomography.

It has also been contemplated that the bed can be used with various other imaging devices such as MRI devices. The bed could be designed such that it attaches to an MM or other imaging device for examination, and then can be detached from the imaging device after the examination. In this way, the patient can remain in the same bed without being moved to a different table or bed for examinations, surgery, or other procedures.

As shown in the example of FIG. 1, the load-bearing structure 40 includes a base 41 suitable to come into contact with the floor and to support the gantry 30. In one embodiment, the structure includes a translating component 43 suitable to move the gantry 30 in a sliding direction 43a substantially parallel to the main direction 20a. In addition, wheels 45 (FIG. 1), which may be pivoting wheels, suitable to roll on the floor 1a when moving the radiological imaging system 1.

In one embodiment, the translating component 43 includes a linear guide 43b suitable to control the translational motion along the sliding direction 43a that is substantially parallel to the direction 20a. The translating component 43 may include a carriage 43c suitable to slide along the linear guide 43b. In one embodiment, the linear guide 43b is motorized. It has been contemplated that any suitable mechanism can be used to move the gantry 30, either manually or mechanically/automatically.

Referring to the example of FIG. 5, one embodiment of the system 1 includes a rotation device 44 suitable to rotate the gantry 30 about an axis of rotation 44a that is substantially perpendicular to the main direction 20a and, specifically, substantially perpendicular to the floor. The rotational device 44 includes a first plate 44b that is integrally attached to the carriage 43c. The rotation device 44 may also include a second plate 44c integrally attached to the gantry 30. In addition, the rotation device 44 may include a rotation component (not shown) that has pins, bearings, or other known mechanical elements suitable to permit the second plate 44c, and thereby the gantry 30, to rotate about the axis of rotation 44a, in relation to the first plate 44b, and therefore to the rest of the radiological imaging system 1. The rotation device 44 also has a control lever 44d, suitable to be held by an operator to control the rotation of the gantry 30 about the axis 44a. A handle or any other type of grip may be used to control the rotation of the gantry 30 about the axis 44a.

In one embodiment, the rotation component and the control lever 44d permit the gantry 30 to be disposed in at least two configurations. One possible configuration is a working configuration where the gantry 30 is substantially perpendicular to the main direction 20a. Another possible configuration is a rest configuration where the gantry 30 is substantially parallel to the main direction 20a. The rotation component and control lever may also permit the gantry to be in a variety of other positions and angles relative to the bed 20.

Figure 2:
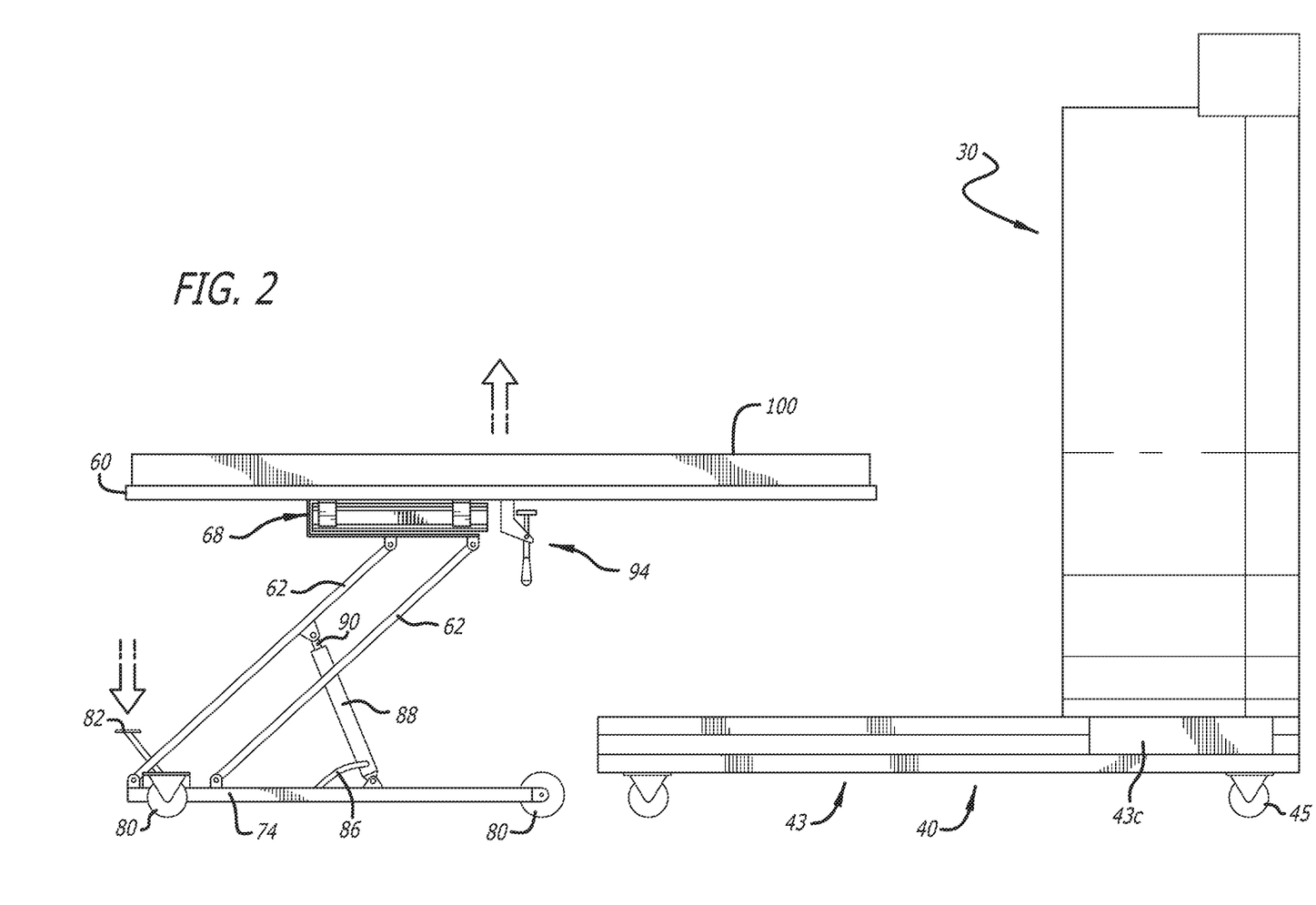
FIG. 2 shows a radiological imaging system with an exemplary bed in a lowered position.
Figure 3:
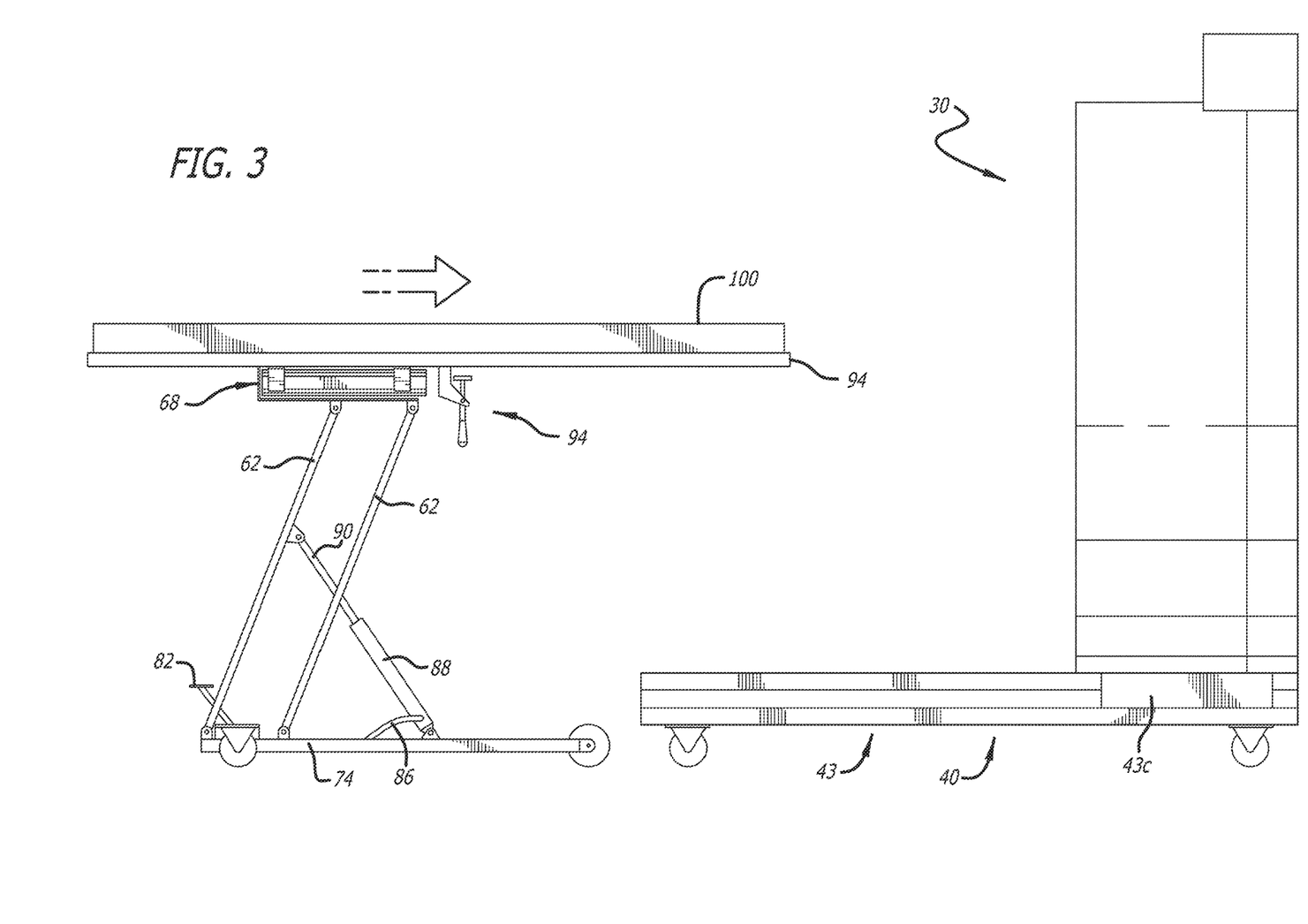
FIG. 3 shows a radiological imaging system with an exemplary bed in a raised position.
Figure 4:
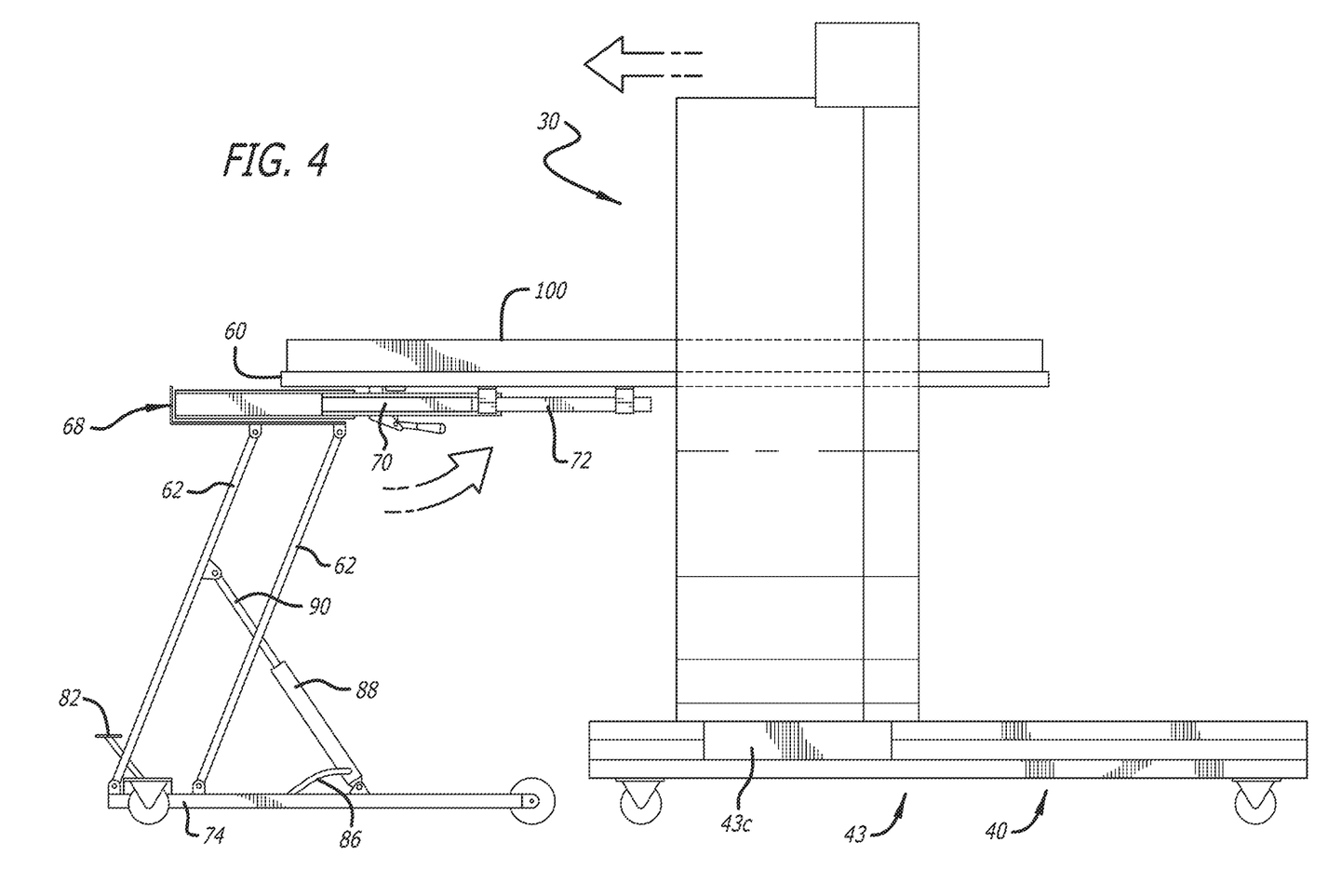
FIG. 4 shows a radiological imaging system with an exemplary bed in a raised position and a table moved in a forward position such that at least a portion of the table is within a gantry of the radiological imaging system.

In one embodiment, the cantilever bed 20 includes a table or table top 60 secured to at least one support member or leg 62 that is hinged to a base 64. As shown in FIGS. 2-4, a surgical table top or mattress 66 may be attached to the top of the table 60. The table 60 is shown to be in a rectangular shape, however, the table may include rounded edges or be in the shape of an oval. The table 60 is secured to slider guides 68 that allow the table 60 to move along the main direction 20a. As best shown in FIG. 4, the slider guides 68 include an outer guide 70 and an inner guide 72 that slides along and extends past the outer guide. In this embodiment, the table 60 is directly or indirectly attached to inner guide 72 in order to move in the Z direction, along the main direction 20a, such that the table 60 may move closer to or farther away from the gantry 30.

By way of example only, the base 64 of the table shown in FIG. 1 includes two side rails 74 and one end rail 76 at a proximal end of the base 64. One or more bars 78 may be used to stabilize the two side rails 74 as shown in FIG. 1. In one embodiment, there is no end rail at the distal end of the base 64, which allows the bed 20 to slide closer to the gantry 30 of the system. In this embodiment, the width of the load bearing structure 40 is less than the width between the two side rails 74 of the base 64 to allow the bed 20 to slide closer to the gantry 30. In another embodiment the base of the bed may slide over the load bearing structure 40. In another embodiment, the base of the bed may slide under the load bearing structure 40. The base 64 of the bed may be attached to the load bearing structure 40. In another embodiment, the base 64 of the bed is not attached to the load bearing structure and is instead locked in place. For instance, the base includes casters or wheels 80 that may be locked to prevent the bed from moving. As shown in the figures, the bed 20 includes four wheels, two at the proximal end and two at the distal end. Any number of wheels may be used, for instance three, with two wheels at the distal end and one while at the proximal end.

The support members or legs 62 of the bed are hingedly attached to the slider guides 68 in one embodiment. In another embodiment, each leg is hingedly attached to a table base attached under the table 60 and the table base includes the slider guides that attached to the table 60. The other ends of the support members or legs 62 are hingedly attached to the base 64. Attaching the legs 62 to the table 60 and the base 64 in this manner allows the table to be raised and lowered. The legs may be attached via screws, bolts, pins, or the like to hinges or other attachment mechanisms on the base 64 and slider guides 68. As shown in FIG. 2, the bed is in a lowered position, which allows a patient to be placed on the bed. Once on the bed, the patient may be raised on the bed into a suitable position for examination as shown in FIG. 3.

In one embodiment, the bed raises using a hydraulic system to raise and lower the height of the bed in the Y axis. The hydraulic system includes a foot pedal 82 that includes a stem that is in contact with a hydraulic pump 84. The hydraulic pump may be attached to one of the bars 78 of the base 64. A hose 86 attached to the hydraulic pump 84 is also in contact with a hydraulic cylinder 88 including a piston 90. One end of the hydraulic cylinder 88 is attached to a bar 78 of the base and the piston 90 of the hydraulic cylinder is attached to a cross bar 92 that extends and is secured between two legs 62 of the bed. When the foot pedal 82 is pumped, the hydraulic pump 84 forces air into the hydraulic cylinder 88 to raise the piston and the height of the bed. In one embodiment, holding the foot pedal 82 down releases air and lowers the bed 20. It has also been contemplated that the bed may be raised or lowered with an electric motor instead of manually with a hydraulic pump. In other embodiments, the bed may be adjusted in any direction using any type of motor, mechanical apparatus, and the like.

As shown in FIG. 2, the bed 20 also includes a slide lock 94 that engages the table 60 and prevents the table from sliding along the slider guides 68. In one embodiment, the slide lock may be an over center lock as shown. In other embodiments, other types of locks, such as pins, straps, screws, or the like, may be used to secure the table in place. FIG. 2 shows the slide lock 94 in an unlocked position allowing the table 60 to slide along the main direction 20a. FIG. 4 shows the slide lock 94 engaged with the table 60 to lock it in place. To engage and disengage the slide lock 94 from the table, an operator simply moves the handle of the slide lock up to lock and down to unlock.

A separate set of slider guides (not shown) may be perpendicular to the slider guides 68 to allow the table 60 to be adjusted along the X axis. The bed 20 may also be moved in the X axis by using the wheels 80 and moving the base. This may be beneficial in order to properly position and adjust a patient with the gantry 30 for examination. It has also been contemplated that the table 60 rotates along the axis of the main direction 20a in order to tilt the patient clockwise or counter-clockwise.

The table 60 of the bed 20 holds a patient and may be adjustable in X, Y, and Z axes. The table 60 may be put through the circular gantry 30 of the imaging system 1 and the base 64 of the bed 20 is configured to slide over or under the imaging device. As shown in FIG. 1, the base 64 of the bed 20 is located at the rear of the gantry 30. The area of the bed 20 that may be in the imaging area of the system 1 may be radiolucent. With the imaging area of the gantry 30 outside the closed ring housing, being projected forward to allow clear side access to the patient, the clinician would have unobstructed access to access three sides of the patient. This may be used for interventional procedures and allow a portable imaging CT/Fluoroscopy device to be used with the gantry in the 90 degree rotated position. As shown in the examples provided in figures, the bed 20 may be positioned adjacent to the gantry 30. In other embodiments, the bed 20 may be attached to the load-bearing structure 40.

The design of this embodiment allows unobstructed access by a clinician for interventional procedures when the patient's region of interest is in the viewing area of a multi-modality imaging device with a circular gantry.

In one embodiment, the bed 20 or, at least portion of the bed is made from a radiolucent or radio-transparent material that is transparent to X-rays. In one embodiment the table 60 is made from a material having reduced Hounsfield units (HU) such as, for instance, a composite material with a polymer matrix and fiber reinforcement, yet more specifically, in carbon fiber or aramid or glass fiber and matrix in epoxy resin or the like. The legs 62 and base 64 of the bed may be made of any material, such as metal, wood, or plastic.

In one embodiment, the bed 20 is radiolucent on at least the cantilevered end and is capable of serving as a critical care bed, spine operative bed, orthopedic surgical table, trauma bed or surgical table. As shown in FIG. 2, the table may include a surgical table top or mattress 100 that is permanently attached to the table or removably attached to the table. Straps or rails may also be attached to the bed 20 in order to secure the patient in place. Any rails may be removable before imaging the patient with imaging device.

In one embodiment, an imaging device may be placed over the patient and be able to translate in the Z axis (along the main direction 20a) as shown in FIG. 3. As described above, the bed is height adjustable and also adjustable along the X and Z axes. The bed may lock into position adjacent to the imaging device, and it is contemplated that the imaging device may lock to the bed 20 such that the device can move relative to the bed in a precise and known position.

This invention allows for patients in trauma centers, emergency departments, surgery suites and ICU areas to be transported to and scanned by a high resolution imaging device that may also connect to other devices such as surgical robotic systems and surgical navigation systems, while staying in a single bed. This invention also will allow a facility to own one imaging device to be used for several beds and not require patients to be moved to a separate bed solely used for imaging. As described herein, the bed 20 may be removed from the imaging device and easily moved to any room of the treatment facility. In this way, a patient on the bed 20 may be transported from an external location, such as a treatment room, trauma room, operating room, or outside of the hospital, to an imaging room so that the bed and be attached to the imaging device. The bed could then be released from the imaging device and surgery could be performed on the patient in the bed or the patient could be moved to a recovery room while remaining in the bed. Portable imaging device also may be transported to the patient in the bed 20, and the bed can be attached to the imaging device for analysis.

In yet another embodiment, the bed 20 is removably attached to the load-bearing structure 40 to permit the bed 20 to be fixed firmly to the structure and then to be released and moved away from the rest of the radiological imaging system 1.

By way of example only, and not by way of limitation, a method of using the radiological imaging system will be described. In one embodiment, the radiological imaging system 1 is in the rest configuration, that is, with the gantry 30 substantially parallel to the direction 20a. At the moment of use, the operator rotates the gantry 30 about the axis of rotation 44a using the control lever 44d so that the radiological imaging system 1 moves into the working configuration where the gantry 30 is substantially perpendicular to the main direction 20a.

With the bed 20 in a lowered configuration as shown in FIG. 2, a patient may be placed on the table 60 (or surgical top 100). In one embodiment, the patient may be placed on the bed from an ambulance and wheeled into a hospital or imaging facility from room to room. Once the patient is on the table 60, an operator may raise the bed to a desired height by pumping the foot pedal 84. The patient may then be transported on the bed to the imaging device. After placing the radiological imaging system 1 in the working configuration, the bed 20 including the patient is moved in position such that the bed 20 is adjacent the imaging device. The wheels 80 of the bed may be locked once the bed is in position. The bed may be adjusted towards the left or right of the gantry 30 in order to center the bed in position. Furthermore, the rails 74 of the base 64 will help line the bed up with the load bearing component 40 of the imaging device. In another embodiment, the bed 20 may be locked onto the load bearing structure of the imaging device. The operator may then adjust the height of the bed (Y axis). As shown in FIG. 3, the slide lock 94 may be unlocked and the table 60 slid forward along the main direction 20a so that the cantilevered table is at least partially in the analysis zone 30a. Once in proper position, the operator may then engage the slide lock 94 with the table 60 to secure its position as shown in FIG. 4. The operator may adjust the bed along the X, Y, and Z axes to better position the area of interest in the analysis zone 30a. At this point, as shown in FIG. 4, the operator uses the control unit to control the translation of the gantry 30 in the sliding direction 43a until the gantry 30 reaches the analysis zone and performs the radiological imaging of the intended portion of the patient.

When the radiological imaging procedure is complete, should the operator deem it necessary to perform a different analysis or procedure, the bed 20 may be adjusted using controls to give the clinician access to the patient without the gantry or other features of the imaging system 1 interfering. Furthermore, the bed 20 may be easily unlocked or detached from the imaging system and moved to allow the clinician to examine the patient. Still further, once the imaging procedure is complete, the bed may be moved into a surgical room or recovery room without moving the patient to another bed. This is possible because the bed 20 functions as a surgical or treatment bed.

In addition, once the bed 20 has been removed from the radiological imaging system 1, the operator, using the rotation device 44, rotates the gantry 30 by means of the control lever, returning the gantry 30 to the rest configuration.

In view of the foregoing description, it can be appreciated that the radiological imaging system 1, by virtue of the multipurpose bed 20, can quickly transport patients to from a patient room, to an imaging room, to a surgical room, and to any other room in the facility without having to move the patient into different beds. Furthermore, it can be appreciated that the bed 20 as described herein is adjustable to better position the patient under the gantry for imaging and also for giving a clinician unfettered access to the patient.

Furthermore, by virtue of the possibility of removing the bed 20 and rotating the gantry 30, it is possible to place the radiological imaging system 1 in the rest configuration in which the gantry positioned parallel to the main direction 20a. In the rest configuration, the radiological imaging system 1 has reduced dimensions and is therefore easy to maneuver compared to the prior art devices.

Variations may be made to the embodiments described herein without departing from the scope of the present disclosure. All the elements described and claimed may be replaced by equivalent elements and the parts, materials, shapes and dimensions may be chosen as needed.

What is claimed:

1. A radiological imaging system comprising:
   a gantry defining an analysis zone in which at least part of a patient is placed, and the gantry is supported by a gantry base;
   a source suitable to emit radiation that passes through the at least part of the patient, the radiation defining a central axis of propagation, and the source housed within the gantry;
   at least one detector suitable to receive the radiation and housed within the gantry;
   a translating component connected to the gantry to translate the gantry in a main direction substantially perpendicular to the central axis of propagation; and
   a bed extending along the main direction and having a table top to support a patient, a bed base separate from the gantry base, at least one support member connected to the table top at a first end and a proximal end of the bed base at a second end, and no support members are connected to a distal end of the bed base, with the bed base in a stationary position, the table top translates along the main direction, and the at least one support member is adjustable to raise and lower the table top.

2. The system of claim 1, wherein the table top translates in a direction perpendicular to the main direction to adjust the position of the table top to the left and right in relation to the gantry.

3. The system of claim 1, wherein a portion of the bed is made of radio-transparent material.

4. The system of claim 1, wherein the bed includes wheels attached to the bed base in order to move the bed.

5. The system of claim 1, wherein the bed includes a surgical top attached to the table top.

6. The system of claim 1, wherein the table top is rotatable around an axis defined by the main direction.

7. The system of claim 1, wherein the bed includes a hydraulic pump that adjusts the at least one support member to raise and lower the table top.

8. The system of claim 7, wherein the hydraulic pump is in communication with a hydraulic cylinder that is attached to the bed base at one end and the at least one support member at the other end.

9. The system of claim 7, wherein the bed includes a foot pedal in communication with the hydraulic pump to raise and lower the table top.

10. The system of claim 1, wherein the table top is attached to a slider guide in order to translate along the main direction.

11. A method of obtaining radiological images of a patient, the method comprising:
    placing the patient on a bed, the bed extending along a main direction and having a table top for a patient, a bed base, and at least one support member connected to the table top at a first end and a proximal end of the bed base at a second end, and no support members are connected to a distal end of the bed base;
    translating the table top along a line parallel to the main direction;
    adjusting the at least one support member to raise and lower a height of the table top;
    emitting radiation from a source of the radiological imaging device to a portion of the patient confined in the bed;
    receiving the radiation using at least one detector, wherein the at least one detector is positioned substantially on an opposite side to the source in relation to the bed; and
    translating a gantry housing the source and at least one detector parallel to the main direction and the gantry is supported by a gantry base separate from the bed base.

12. The method of claim 11, further comprising translating the table top in a direction perpendicular to the main direction along a Y axis.

13. The method of claim 11, further comprising moving the bed into position adjacent to the gantry and translating the table top in a direction parallel to the main direction in order to place at least a portion of the patient on the table top within the gantry.

14. The method of claim 11, further comprising tilting the table top around an axis defined by the main direction.

* * * * *